United States Patent [19]

Proehl et al.

[11] Patent Number: 5,612,173
[45] Date of Patent: Mar. 18, 1997

[54] ONE EQUIVALENT COUPLERS AND LOW PKA RELEASE DYES

[75] Inventors: Gary S. Proehl, Rochester; Stephen P. Singer, Spencerport; J. Michael Buchanan, Rochester, all of N.Y.

[73] Assignee: Eastman Kodak Company, Rochester, N.Y.

[21] Appl. No.: 449,891

[22] Filed: May 23, 1995

Related U.S. Application Data

[63] Continuation of Ser. No. 897,713, Jun. 12, 1992, abandoned.

[51] Int. Cl.$^6$ ........................................ G03C 1/46
[52] U.S. Cl. ................ 430/504; 430/543; 430/559; 430/955; 430/958; 430/226
[58] Field of Search .................. 430/559, 543, 430/226, 958, 955, 504

[56] References Cited

U.S. PATENT DOCUMENTS

| | | | |
|---|---|---|---|
| 1,921,545 | 8/1933 | Seymour | 95/8 |
| 2,083,672 | 6/1937 | Seymour | 95/9 |
| 3,884,625 | 5/1975 | Kalopissis et al. | 8/10 |
| 4,248,962 | 2/1981 | Lau | 430/382 |
| 4,474,867 | 10/1984 | Naito et al. | 430/543 |
| 4,711,837 | 12/1987 | Ichijima et al. | 430/548 |
| 4,840,884 | 6/1989 | Mooberry et al. | 430/557 |
| 4,923,789 | 5/1990 | Yagihara et al. | 430/517 |
| 4,975,361 | 12/1990 | Sato et al. | 430/559 |
| 5,100,759 | 3/1992 | Sato et al. | 430/559 |

FOREIGN PATENT DOCUMENTS

| | | |
|---|---|---|
| 0173302 | 3/1986 | European Pat. Off. . |
| 0313308 | 4/1989 | European Pat. Off. . |
| 2359132 | 3/1978 | France . |
| 6249348 | 3/1987 | Japan . |
| 63-202745 | 8/1988 | Japan . |
| 3-83688 | 4/1991 | Japan . |
| 3-83687 | 4/1991 | Japan . |
| 3-83689 | 4/1991 | Japan . |

OTHER PUBLICATIONS

Patent Abstracts of Japan, 63 202 745 (Fuji), vol. 12:804, (1988).
C. E. Kohrt, Research Disclosure, "Thermal Silver–dye Bleach Element And Process", vol. 181:269–271 (1979).

*Primary Examiner*—Geraldine Letscher
*Attorney, Agent, or Firm*—Arthur E. Kluegal

[57] ABSTRACT

A photographic element containing a dye which when released from a coupler has a sufficiently low pKa, generally less than about 5, such that the dye remains substantially or fully ionized during coating of the film and in the produced film, results in an element containing a dye which has the desired hue without the use of additional additives, such as mordants, to keep the dye ionized. The dye is also useful in photographic elements without release from a coupler, for example, as a filter dye.

28 Claims, No Drawings

ONE EQUIVALENT COUPLERS AND LOW PKA RELEASE DYES

This application is a continuation, of application Ser. No. 07/897,713, filed Jun. 12, 1992.

BACKGROUND OF THE INVENTION

This invention pertains to silver halide photographic materials, in particular to low pKa release dyes which are useful as the releasable portion of a coupler, wherein the coupler is a one-equivalent coupler. The dyes, when attached to coupler moieties, are also useful as masking couplers in photographic elements. The dyes are also useful as filter dyes in photographic elements.

For economic reasons, it is desirable in the photographic art to reduce the amount of silver used during processing. One way to reduce the use of silver is to use one-equivalent dyes or couplers, which result in the formation of two dye moieties from development of two molar equivalents of silver. Examples of various one-equivalent couplers are found in U.S. Pat. No. 4,840,884 and European Patent Application 173,302. These one equivalent couplers usually do not remain ionized after the film is processed.

The tendency of a dye to remain ionized is related to its acidity, of which the pKa value is a measure. Although, strictly speaking, pKa values relate to dilute aqueous conditions and thus cannot be determined for many hydrophobic photographic dyes, a closely related acidity scale can be constructed using aqueous micelles of a nonionic surfactant, such as Triton X-100 as the reference condition, instead of water. A procedure for acidity determinations in micelles is given in Example 4, and the term pKa used hereinafter refers to acidities determined in such a micelle medium.

As previously mentioned, one-equivalent couplers generally produce an ionizable dye. The dyes have a high pKa, that is, greater than about 5, such that the dye does not ordinarily remain completely ionized after the film is processed. These dyes have disadvantages because partial protonation of the auxochromic group can occur during or after processing. Such protonation may lead to a shift in hue. This shift in hue occurs particularly in dyes with an oxygen/hydroxyl auxochrome, because these dyes have a different hue depending on whether they are ionized or not. These dyes are known as indicator dyes.

To prevent this undesirable shift in hue caused by the dye not remaining fully ionized in the film, it is often necessary to use mordants or a special cation to keep the auxochromic group of the dye fully ionized at a typical gel (film) coating having a pH of about 5.7.

A mordant is known in the art as a material, such as a polymer, which complexes or absorbs the dye and stabilizes the ionized form. However, the use of mordants is not always acceptable because they often have undesirable affects on other photographic properties, such as the reduction of the rate of bleaching and/or fixing, as well as the retention of materials such as sensitizing or filter dyes, which normally wash out of the film.

Low pKa azo dyes have been described in EP-173,302, U.S. Pat. Nos. 4,248,962 and 4,711,837 and Japanese Kokai 63-202745. However, there has not been described in the art other types of dyes which have a low pKa and thus remain fully ionized in film, and which can be released upon reaction of a one-equivalent coupler with oxidized silver halide.

U.S. Pat. No. 4,923,789 discloses structures A–B, where A is a blocking group and B is a dye, particularly a diffusible dye. However, low pKa dyes such as disclosed hereinafter are not suggested.

Thus, there has been a need to provide a photographic element comprising a low pKa dye which can be released from a coupler. There is also a need to provide a one-equivalent coupler which can release such a dye so as to limit the amount of silver halide required during developing. There has also been a need to provide a releasable dye which is useful in photographic films, wherein the dye remains substantially ionized or completely ionized during the coating of the film and in the produced film, without the need of mordants and/or other ion-stabilizing additives. There also has been a need to provide a low pKa dye which is useful in photographic elements, particularly as a filter dye, without the necessity of being released from a releasing compound such as a coupler.

SUMMARY OF THE INVENTION

These and other needs have been satisfied by providing, in accordance with one aspect of the invention, a dye useful in a photographic element having the structure:

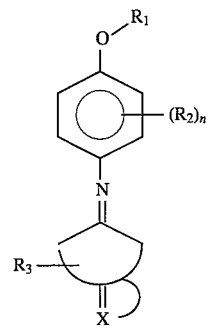

Wherein, $R_1$=H, a removable timing group, or a removable blocking group, wherein removable denotes that after processing $R_1$ is hydrogen so that the dye remains substantially or completely ionized in the element, $R_2$=one or more substituents which ensure that the oxygen auxochrome group remains ionized after processing of the element, n=1 to 4, wherein if n=2, 3, or 4 then the $R_2$ groups may be the same or different, $R_3$=one or more substituents which may be located anywhere along the ring or ring system, X=O or N; wherein if X is N then it is part of a heterocyclic ring system that forms part of the dye chromophore,

represents a carbon containing ring or ring system, with the proviso that the substituents $R_2$ and $R_3$ and the ring or ring system are selected so that the dye has a low enough pKa so that it remains fully ionized or substantially ionized in the element.

There is also provided, in accordance with another aspect of the invention, a molecule which may act as a one-equivalent coupler or a masking coupler, having the structure:

COUP—[CONNECT]$_n$—[T]$_m$—DYE

Wherein, n is 0 or 1, m is 0, 1, or 2,

COUP is a coupler moiety,

CONNECT is a group attached to a coupling site of the coupler that connects the coupler to either the timing group T or directly to the dye, if attached directly to the dye it preferably remains permanently attached to the dye after the dye is released from COUP, T is a timing group, which is cleaved from the dye during processing, DYE is a dye as described above having a low pKa upon release such that the DYE remains substantially or completely ionized in the element, wherein the molecule optionally contains one or more ballast groups.

There is also provided, in accordance with the invention, a photographic element comprising a support and a silver halide emulsion layer having associated therewith a dye or molecule having the structure described above.

There is further provided a multicolor photographic element comprising a support bearing a cyan dye image-forming unit comprising at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler and a yellow dye image-forming unit comprising at least one blue-sensitive silver halide emulsion layer having associated therewith at least one yellow dye-forming coupler, wherein the element further comprises a dye or molecule having the above structure.

There is also provided a process for developing an image in a photographic element comprising a support and a silver halide emulsion containing an image-wise distribution of developable silver halide grains, said process comprising the step of developing said element with a silver halide color developing agent in the presence of a dye or molecule having a structure described above.

It is also an object of the present invention, to provide a photographic silver halide emulsion containing the dye described above and/or the molecule described above which releases the dye.

It is further an object of the present invention to provide a method of using the above dye as a filter dye in a photographic element.

Further objects, features, and advantages of the present invention will become apparent from the detailed description of preferred embodiments that follows.

DETAILED DESCRIPTION OF THE PREFERRED EMBODIMENTS

The dyes of the present invention are of the following formula:

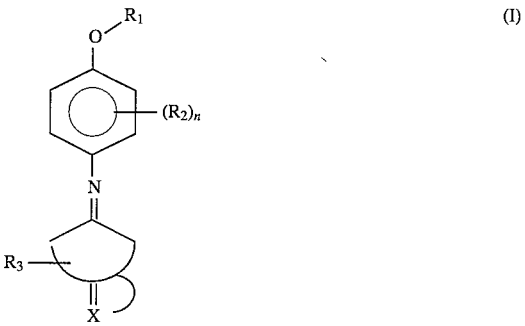

Wherein, $R_1$=H, a removable timing group, or a removable blocking group, with the proviso that after processing, that is, after removal of the timing or blocking group, $R_1$ is hydrogen, so that the dye remains ionized in the film.

Removable means that the group is detached from the oxygen during conventional C-41 processing or other processing.

Blocking groups are known in the photographic art as groups used to inactivate, protect or otherwise modify the properties of a functional group or substituent. The release of the groups is generally non-imagewise (that is, it does not require oxidized developer), and the rate of release is generally not important, so long as it is completed within the appropriate time scale. Useful removable blocking groups are any known in the art and include carbonyl compounds, such as

where R is a substituted or unsubstituted alkyl, alkyloxy, or aromatic ring, for example,

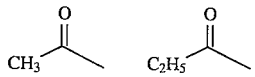

benzoate, and p-nitrobenzoate. For examples, see U.S. Pat. No. 5,051,343; 4,446,216; 4,554,243; 2,860,974; 4,690,885; 4,358,525; 4,554,243; GB 2,036,994; and U.K. Application No. 2,105,482. Particularly useful are those based on dinucleophile release (hydroxylamine or peroxide) such as described in U.S. Pat. No. 5,019,492.

Timing groups are known in the art as groups used to inactivate or modify the properties of a compound or photographically useful group (PUG), such as a dye. The release of a timing group bonded to a PUG from a carrier compound, such as a coupler, is generally, although not always, image-wise and the rate of release of the PUG is critical to its function. Useful timing groups include all those known in the art, and particularly those described hereinafter in the description of the T groups in a molecule of structure II.

$R_2$=a substituent, located in the 2, 3, 5, or 6 position which ensures that the O—$R_1$ group remains ionized during and after coating of the film. Particularly, the number and type of $R_2$ groups are selected so that the auxochromic group of the dye remains ionized in the coated film. These groups are preferably selected from any known electron withdrawing groups, and are preferably present in both the 2 and 6 positions Preferred electron withdrawing groups include nitro, Cl, CN, $SO_2N(R)_2$, $CON(R)_2$, $CO_2R$, wherein R is an alkyl or aryl group, preferably having 1 to 20 carbon atoms, or a hydrogen atom, a preferred R group being a tertiary butyl group. Preferred $R_2$ groups include Cl, $SO_2NH(t-Bu)$, and $C(O)NH_2$.

n=1 to 4.

$R_3$=one or more substituents, which may be located anywhere along the ring or ring system described below. Any known substituent can be used so long as the dye has the inventive low pKa. Preferred substituents are as described in structures 2–5 which follow.

X=O or N; if N, then it is part of the ring or ring system described below, resulting in a heterocyclic ring, wherein the N is part of the ring system that forms part of the dye chromophore.

The

indicates that if X is N, then it is part of the ring as described above.

represents a carbon containing ring or ring system, which may comprise fused or bridged rings. When the dye is cyan, preferred rings include phenyl and naphthyl rings. The ring or ring system may contain any suitable substituents $R_3$ and the ring may comprise various heterocyclic atoms, with the proviso that if X is nitrogen, it is part of the heterocyclic ring. If the ring is a heterocyclic ring, it is preferably a bicyclic system that contains at least two N atoms, and is most preferably a pyrazolotriazole.

The substituents $R_2$ and $R_3$ are selected so that the dye has a low enough pKa so that it remains fully ionized or substantially ionized in the coated film. By "substantially ionized" it is meant that the dye is ionized sufficiently so that there is no readily detectable shift in hue of the dye after processing. Generally, the pKa is below about 5, and more preferably below about 4.

Generally speaking, to lower the pKa of the auxochromic oxygen, one can do one or more of the following:

a) put electron-withdrawing groups in conjugation with the auxochrome, these groups include classical electron withdrawing groups such as cyano, sulfone, etc., in ortho and/or para positions, or electronegative groups, such as methoxy, in the meta position;

b) increase the electron-withdrawing and decrease the electron-donating ability of the conjugated groups by appropriate H-bonding. For example, the H-bonding group in $R_7$ of structure 3 makes the imino nitrogen a better electron withdrawing group. H-bonding to the carbonyl oxygen by $R_4$ in structure 2, or H-bonding to the ortho oxygen in structure 4 should also work to lower the pKa of the auxochromic oxygen.

c) H-bond to the auxochromic oxygen itself, d) increase the overall chromophore size, and/or e) choose more electron-withdrawing substituents and ring systems, since the more electron-withdrawing these are, the more likely it is that the dye will remain ionized.

Based on the above generalities and the knowledge of a person having ordinary skill in the art, such a person would be able to select the substituents and the ring system so that the dye has the desired pKa.

More preferred dyes include the following, which have structures 2–5 set forth below. In these structures, R' is a substituted or unsubstituted alkyl group or a substituted or unsubstituted phenyl group or a hydrogen atom. The alkyl groups preferably have 1 to 20 carbon atoms and the alkyl and phenyl group may optionally be substituted with any desired substituents, such as substituents having 1 to 20 carbon atoms. The alkyl and phenyl groups may contain linkages other than carbon atoms including O, $SO_2$, or N linkages. $R_1$ and $R_2$ are as defined above in connection with structure I.

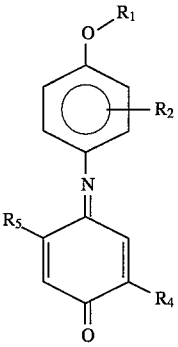

Wherein, $R_4$ and $R_5$ are substituents within the scope of $R_3$, previously defined, and are preferably —NHCOR' or —NHCON(R')$_2$.

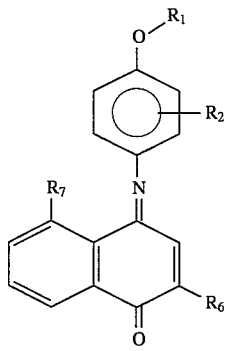

Wherein, $R_6$ is an electron withdrawing group. These groups are as discussed for $R_2$ and are preferably selected from Cl, $SO_2N(R')_2$, CN, $SO_2R'$, $CON(R')_2$, $CO_2R'$, and CONHR'.

$R_7$=H or a group capable of hydrogen bond donation to the imine nitrogen, such as OH or an NH acidic group including —NHCOR', —NHCON(R')$_2$, —NHSO$_2$R', —NHSO$_2$N(R')$_2$. H-bond donating groups are more preferred than hydrogen.

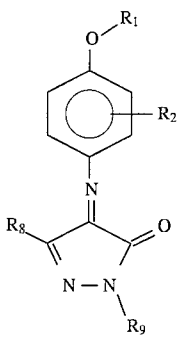

(4)

Wherein, $R_8$=$NR'_2$, NH—Ph—R', NHCOR', or NH—Ph—NH—SO$_2$R'

$R_9$=a substituted phenyl group. Suitable substituents include any known in the art, such as alkyls, alkyloxys, and halides such that they do not adversely affect the use of the dye in photographic elements. Chlorine is a preferred substituent.

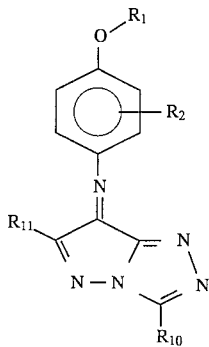

(5)

Wherein, $R_{10}$ and $R_{11}$ are independently selected from a substituted alkyl, substituted alkoxy, or substituted phenyl group. Suitable substituents for $R_{10}$ and $R_{11}$ include methyl, ethyl, t-butyl, p-methoxyphenyl, methoxy, ethoxy, and for $R_{11}$—NH—CO—R' groups.

Preferred substituents for $R_{11}$ are methyl and —NH—CO—$R_1$. Dyes 2 and 3 are cyan dyes and dyes 4 and 5 are magenta dyes. Especially preferred cyan dyes fall within generic structure 3 and have the structure:

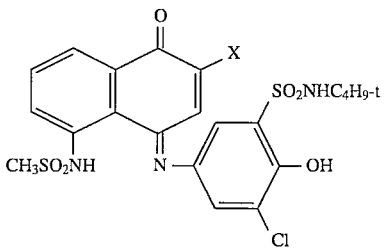

(6)

Wherein,

X=—CONHR' or —SO$_2$N(R')$_2$

The dyes of structure 6 are anionic cyan dyes which, when either protonated or blocked on the chromophore, are shifted hypochromically in their absorption.

The dyes of the present invention are especially useful when used in a photographic element and released from a coupler. The coupler is either directly attached to the dye, preferably to the auxochromic oxygen, or indirectly attached through a connecting group, or through a timing group that is cleaved from the dye during processing, or through both a timing and connecting group. Upon release from the coupler, the dyes are substantially or completely ionized in the film without the use of a mordant. To remain ionized in the film, the dyes generally must have a pKa of less than about 5, and preferably less than about 4. This is because the film during coating generally has a pH of about 5.7 and the finished film generally has a pH of about 6 to 7.5.

A preferred structure of the molecule which releases the dye is represented by the following structure (II):

$$\text{COUP}-[\text{CONNECT}]_n-[T]_m-\text{DYE} \qquad (II)$$

Wherein, n is 0 or 1, m is 0, 1, or 2

COUP is a coupler moiety,

CONNECT is a group attached to a coupling site of the coupler that connects the coupler to either the timing group T or directly to the dye, if it is a group attached directly to the dye it preferably remains permanently attached to the dye after the dye is released from COUP, T is a timing group which is cleaved from the dye during processing, DYE is a dye having a low pKa upon release and having a structure falling within generic structure I previously described.

The DYE is generally selected from the cyan, magenta, and yellow dyes.

The COUP moiety can be derived from any couplers known in the art. Cyan, magenta, and yellow dye forming coupler moieties are useful, as are those which yield a colorless product or black dye upon development. The COUP can be selected so that it forms a dye upon reaction with oxidized silver halide which is the same or a different color from the DYE released. A listing of patents and publications from which useful coupler moieties can be selected follows.

Couplers which form cyan dyes upon reaction with oxidized color developing agents are described in such representative patents and publications as: U.S. Pat. Nos. 2,367,531; 2,423,730; 2,474,293; 2,772,162; 2,801,171; 2,895,826; 3,002,836; 3,034,892; 3,041,236; 3,419,390; 3,476,563; 3,772,002; 3,779,763; 3,996,253; 4,124,396; 4,254,212; 4,296,200; 4,333,999; 4,443,536; 4,457,559; 4,500,635; 4,526,864; 4,690,889; 4,775,616; and "Farbkuppler-eine Literaturubur-sicht," published in Agfa Mitteilungen, Band III, pp. 156–175 (1961). Such couplers typically are phenols and naphthols.

Couplers which form magenta dyes upon reaction with oxidized color developing agents are described in such representative patents and publications as: U.S. Pat. Nos. 1,269,479; 2,311,082; 2,343,703; 2,369,489; 2,600,788; 2,908,573; 3,061,432; 3,062,653; 3,152,896; 3,519,429; 3,725,067; 3,935,015; 4,120,723; 4,443,536; 4,500,630; 4,540,654; 4,581,326; 4,774,172; European Patent Applications 170,164; 177,765; 240,852; 284,239; 284,240; and "Farbkuppler-eine Literaturüberischt," published in Agfa Mitteilungen, Band III, pp. 126–156 (1961). Typically, such couplers are pyrazolones, pyrazolotriazoles, pyrazolobenzimidazoles, or indazoles. Especially useful couplers are pyrazolotriazoles of the category 1H-pyrazolo (1,5-b) (1,2,4) triazole and 1H-pyrazolo (2,3-c) (1,2,4) triazole.

Couplers which form yellow dyes upon reaction with oxidized color developing agents are described in such representative patents and publications as: U.S. Pat. Nos. 2,298,443; 2,407,210; 2,875,057; 3,048,194; 3,265,506;

3,384,657; 3,415,652; 3,447,928; 3,542,840; 3,894,875; 3,933,501; 4,022,620; 4,046,575; 4,095,983; 4,182,630; 4,203,768; 4,221,860; 4,326,024; 4,401,752; 4,443,536; 4,529,691; 4,587,205; 4,587,207; 4,617,256; European Patent Application 296,793; and "Farbkupplereine Literaturübersicht," published in Agfa Mitteilungen, Band III, pp. 112–126 (1961). Typically, such yellow dye forming couplers are acylacetamides, such as benzoylacetanilides and pivalylacetanilides.

Couplers which form colorless products upon reaction with oxidized color developing agents are described in such representative patents as: U.K. Patent No. 861,138; U.S. Pat. Nos. 3,632,345; 3,928,041; 3,958,993; and 3,961,959.

Couplers that form black dyes upon reaction with oxidized color developing agents are described in such patents as U.S. Pat. Nos. 1,939,231; 2,181,944; 2,333,106; and 4,126,461; and German OLS Nos. 2,644,194 and 2,650,764.

It is especially preferred to use a universal coupler. A universal coupler is a material which can react with oxidized color developers to produce a colorless product, or a material which reacts with oxidized color developers to produce a colored compound which is soluble in developer solution and which is washed out of the film during photographic processing.

Preferred universal coupler moieties have the generic structure

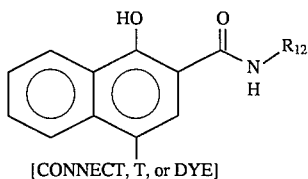

[CONNECT, T, or DYE]

wherein $R_2$ represents a hydrogen atom, or an alkyl, aryl, or heterocyclic group. Preferred $R_{12}$ groups include H, $CH_3$, $CH_2CH_2CO_2H$, $CH_2CH_2CO_2CH_2CH_3$, $CH_2CO_2H$, $CH_2CO_{CH2}CH_3$, $CH_2CO_2CH_3$, $CH_2CH_2CO_2CH_3$, and $CH_2CH_2OCH_3$.

Examples of preferred universal coupler moieties are disclosed in U.S. Pat. No. 4,482,629.

Connecting groups are groups used to connect the COUP with either TG or DYE. Any connecting group known in the art may be used, examples of which include the following:

wherein Y is a heteroatom, such as oxygen, which is attached to the coupling site of COUP, and X is DYE or T, as in structure II.

Any timing group which is known in the photographic art is useful as the timing groups T. Exemplary timing groups T are disclosed in U.S. Pat. Nos. 4,248,962, 4,772,537 and 5,019,492, and European Patent Application No. 255,085. Up to 2 timing groups can be joined sequentially (that is, m of structure II is 0 to 2). The

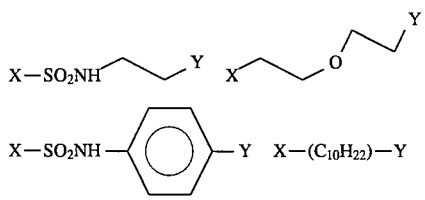

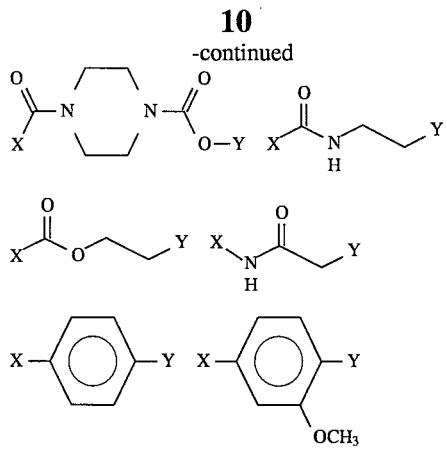

timing group can be unballasted or ballasted, and can contain solubilizing groups.

Preferably, there is at least one ballast group on the molecule represented by (II). The ballast group can be attached to any of the COUP, T, DYE, or CONNECT groups, or a ballast can be attached to more than one of these groups. Preferably, a ballast is attached to DYE, or a part of the molecule which remains attached to DYE, and to COUP or a part of the molecule which remains attached to COUP if the molecule is to act as a one-equivalent coupler. If the molecule acts as a masking coupler, then a ballast is preferably attached to the COUP part of the molecule, or a part of the molecule which remains attached to COUP. Specifically, a ballast group will remain attached to the part of the molecule which is intended to remain in the film after reaction with oxidized silver halide developer. A ballast group is preferably not attached to the part of the molecule which is preferably washed out of the film, such as DYE if the molecule is to act as a masking coupler.

The ballast can be any group of sufficient size and bulk that, with the remainder of the molecule, renders the unreacted molecule immobile, or non-diffusible in the film element prior to processing. It can be a relatively small group if the remainder of the group is relatively bulky. Preferably, the ballast is an alkyl or aryl group containing about 8 to 30 carbon atoms. These groups can be substituted with groups which, for example, enhance the nondiffusibility of the coupler prior to development, or unsubstituted. The ballast can be attached in any way to the molecule. The ballast can also contain additional solubilizing groups such as carboxylic acids or sulfonamides. Suitable ballast groups are described in, for example, U.S. Pat. Nos. 4,420,556 and 4,923,789, which are incorporated herein by reference.

In conjunction with a coupler parent, COUP, use of the dyes of the present invention allows for the preparation of one-equivalent couplers. The dyes, upon release, have a sufficiently low pH such that at the pH present during coating of the film, generally about 5.7, and in the developed film, generally about 6.0–7.5, these dyes are fully or substantially ionized and maintain their desired color, that is, cyan, magenta, or yellow. As such, they require no additives or stabilizers to maintain their correct hue. Specifically, a low pKa is advantageous because it allows the dye to remain fully ionized in the coating without the need of any specialized additives such as a mordant or cation to keep the auxochromic phenol group fully ionized during and after film coating. Thus, the spectral absorption is desirably bathochromic without requiring undesirable additives.

When released, the dyes preferably have a pKa value of less than about 5.0. If the pKa is too high, that is, above about 5, then partial protonation of the phenol group can occur in the coating which may lead to undesirable shifts in hue.

The dyes of the present invention are azophenols which are derived from substituted aminophenols. They do not contain azo groups in conjugation with the auxochromic oxygen. When used as a one-equivalent coupler, DYE is preferably attached to the rest of the molecule (II), through the auxochrome, that is, the O—$R_1$ group of structure (I).

The dyes of the present invention are also useful in combination with a masking coupler, which may be blocked or unblocked. When used as a masking coupler, the component will have the same basic structure as shown above as structure (II).

When used as a masking coupler, the dye may be attached to the CONNECT, T, or COUP at any location, except through the auxochrome of the dye. The auxochromic group of the dye may be blocked by any removable group known in the art. The hue shift can then be controlled by blocking and unblocking the dye, so that the desired masking effect is obtained without absorption of unwanted light which often results in a speed loss in the color of the absorbed light. The blocking group may be any group which is removable during processing. Examples of useful blocking groups are disclosed in UK Patent Application 2,105,482, with particularly effective blocking groups described in U.S. Pat. No. 5,019,492 which is incorporated herein by reference in its entirety.

The molecules (II) of the present invention which release low pKa dyes can be incorporated into photographic elements, wherein during development the low pKa dye is released.

It is also useful to incorporate the dyes by themselves, that is, not attached to COUP, into a photographic element. Specifically, the dyes can be used as filter dyes. Filter dyes are dyes included in a film package to absorb unwanted light. For example, red light sensitized emulsions generally are partially sensitive to blue and green light; it is common practice to coat a magenta filter dye just above the red layer to avoid having excess green light expose the red layer, since the magenta dye absorbs green light. These filter dyes simply absorb light; no coupling is involved. It is preferred to have the filter dyes wash out of the film during processing, although this is not necessary. The filter dyes must remain where they are coated prior to processing, so that they are generally either ballasted, or are used in the form of a solid particle dispersion.

Filter dyes according to the present invention are of the following structures:

DYE-BALLAST (III)

Wherein,

DYE is as described above in connection with structure (II),

BALLAST is a ballast group, such as described above, with the proviso that ballast is not attached to the DYE auxochrome.

Due to the presence of the BALLAST these dyes do not wash out of the film, and remain where they are coated.

Alternatively, filter dyes which wash out of the film during processing have the structure:

DYE-SG (IV)

Wherein,

DYE is as described above,

SG is a solubilizing group not attached to the DYE auxochrome, such as —$CO_2H$, —$SO_3H$, —$NHSO_2$, and —OH.

The SG ensures that the DYE is soluble in the processing solutions, such that the compound washes out of the film during processing.

A filter dye which washes out of the film during processing may also have the structure:

DYE-SL-BALLAST (V)

Wherein,

DYE and BALLAST are as defined above,

SL is a splittable linking group not attached to the auxochrome of DYE which cleaves the BALLAST from the DYE during or after processing, such that DYE is no longer kept in place in the film by the BALLAST.

Suitable SL groups are disclosed in U.S. Pat. No. 5,019,492 and U.S. Pat. No. 5,051,343. A solubilizing group, SG, can also be attached to DYE in the above structure, so as to facilitate removal of the DYE.

The coupler having the structure II can be incorporated in the photographic element in a silver halide emulsion or adjacent to a silver halide emulsion where, during development, the coupler will be in reactive association with development products, such as an oxidized color developing agent.

The photographic elements in which the dyes and couplers of this invention are employed can be either single color or multicolor elements. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. When used as a masking coupler, the masking coupler is located in a layer of the film which is intended to be masked. When used as a one-equivalent coupler, it will generally be located in a layer wherein the released low pKa dye will be useful, such as a layer where the silver level is desired to be minimized. When used as a filter dye, the dye can be used in any layer of a film, so long as the desired filtering effect is obtained.

A typical multicolor photographic element comprises a support bearing a cyan dye image-forming unit comprising at least one red-sensitive silver halide emulsion layer having associated therewith at least one cyan dye-forming coupler, a magenta image forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

In the following discussion of suitable materials for use in the emulsions and elements according to the invention, reference will be made to Research Disclosure, December 1989, Item 308119, published by Kenneth Mason Publications, Ltd., Emsworth, Hampshire P010 7DQ, U.K., the disclosures of which are incorporated in their entireties herein by reference. This publication will be identified hereafter as "Research Disclosure". The elements of the invention can comprise emulsions and addenda described in these publications and publications referenced therein.

The silver halide emulsions employed in the elements according to the invention can comprise silver bromide, silver chloride, silver iodide, silver chlorobromide, silver chloroiodide, silver bromoiodide, silver chlorobromoiodide or mixtures thereof. The emulsions can include silver halide grains of any conventional shape or size. Specifically, the emulsions can include coarse, medium, or fine silver halide grains. High aspect ratio tabular grain emulsions are specifically contemplated, such as those disclosed by Mignot, U.S. Pat. No. 4,386,156; Wey, U.S. Pat. No. 4,399,215; Maskasky, U.S. Pat. No. 4,400,463; Wey et al., U.S. Pat. No. 4,414,306; Maskasky, U.S. Pat. No. 4,414,966; Daubendiek et al., U.S. Pat. No. 4,424,310; Solberg et al., U.S. Pat. No. 4,433,048; Wilgus et al., U.S. Pat. No. 4,434,226; Maskasky, U.S. Pat. No. 4,435,501; Evans et al., U.S. Pat. No. 4,504,570; and Daubendiek et al., U.S. Pat. Nos. 4,672,027 and 4,693,964. Also specifically contemplated are those silver bromoiodide grains with a higher molar proportion of iodide in the core of the grain than in the periphery of the grain, such as those described in U.K. Patent No. 1,027,146; Japanese Patent 54/48521; U.S. Pat. Nos. 4,379,837; 4,444,877; 4,565,778; 4,636,461; 4,665,012; 4,668,614; 4,686,178; and 4,728,602; and in European Patent 264,954. The silver halide emulsions can be either monodisperse or polydisperse as precipitated. The grain size distribution of the emulsions can be controlled by silver halide grain separation techniques or by blending silver halide emulsions of differing grain sizes.

Sensitizing compounds, such as compounds of copper, thallium, lead, bismuth, cadmium and Group VIII noble metals, can be present during precipitation of the silver halide emulsion.

The emulsions can be surface-sensitive emulsions, that is, emulsions that form latent images primarily on the surfaces of the silver halide grains, or internal latent image-forming emulsions, that is, emulsions that form latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

The silver halide emulsions can be surface sensitized, noble metals (for example, gold), middle chalcogen (such as sulfur, selenium or tellurium), and reduction sensitizers, employed individually or in combination, are specifically contemplated. Typical chemical sensitizers are listed in Research Disclosure, Item 308119, Section III.

The silver halide emulsions can be spectrally sensitized with dyes from a variety of classes, including the polymethine dye class, which includes the cyanines, merocyanines, complex cyanines and merocyanines (such as tri-, tetra- and polynuclear cyanines and merocyanines), oxonols, hemioxonols, styryls, merostyryls and streptocyanines. Illustrative spectral sensitizing dyes are described in Research Disclosure, Item 308119, Section IV and the publications cited therein.

Suitable vehicles for the emulsion layers and other layers of elements according to the invention are described in Research Disclosure, Item 308119, Section IX and the publications cited therein.

The photographic elements according to the invention can include additional couplers such as those described in Research Disclosure Section VII, paragraphs D–G and the publications cited therein. These additional couplers can be incorporated as described in Research Disclosure Section VII, paragraph C and the publications cited therein. The coupler combinations according to the invention can be used with colored masking couplers such as described in U.S. Pat. No. 4,883,746, with image modifying couplers such as described in U.S. Pat. Nos. 3,148,062; 3,227,554; 3,733,201; 4,409,323; and 4,248,962 and with couplers that release bleach accelerators such as described in European Patent Application 193,389.

A photographic element according to the invention, or individual layers thereof, can also include any of a number of other well-known additives and layers. These include, for example, optical brighteners (see Research Disclosure Section V), anti-foggants and image stabilizers (see Research Disclosure Section VI), light-absorbing materials such as filter layers of intergrain absorbers, and light-scattering materials (see Research Disclosure Section VIII), gelatin hardeners (see Research Disclosure Section X), oxidized developer scavengers, coating aids and various surfactants, overcoat layers, interlayers, barrier layers and anti-halation layers (see Research Disclosure Section VII, paragraph K), anti-static agents (see Research Disclosure Section XIII), plasticizers and lubricants (see Research Disclosure Section XII), matting agents (see Research Disclosure Section XVI), anti-stain agents and image dye stabilizers (see Research Disclosure Section VII, paragraphs I and J), development-inhibitor releasing couplers and bleach accelerator-releasing couplers (see Research Disclosure Section VII, paragraph F), development modifiers (see Research Disclosure Section XXI), and other additives and layers known in the art.

The photographic elements according to the invention can be coated on a variety of supports as described in Research Disclosure Section XVII and the references cited therein. These supports include polymeric films, such as cellulose esters (for example, cellulose triacetate and diacetate) and polyesters of dibasic aromatic carboxylic acids with divalent alcohols (such as polyethylene terphthalate), paper, and polymer-coated paper.

Photographic elements according to the invention can be exposed to actinic radiation, typically in the visible region of the spectrum, to form a latent image as described in Research Disclosure Section XVIII, and then processed to form a visible dye image as described in Research Disclosure Section XIX. Processing to form a visible dye image includes the step of contacting the element with a color developing agent to reduce developable silver halide and oxidize the color developing agent. Oxidized color developing agents in turn reacts with the coupler to yield a dye.

Preferred color developing agents are p-phenylene diamines. Especially preferred are 4-amino-3-methyl-N,N-diethylaniline hydrochloride, 4-amino-3-methyl-N-ethyl-N-β-(methanesulfonamido) ethylaniline sulfate hydrate, 4-amino-3-methyl-N-ethyl-N-βhydroxyethylaniline sulfate, 4-amino-3-β-(methanesulfonamido)ethyl-N,N-diethylaniline hydrochloride and 4-amino-N-ethyl-N-(2-methoxyethyl)-m-toluidine-di-p-toluenesulfonic acid.

With negative-working silver halide, the process step described above leads to a negative image. The described elements are preferably processed in the known C-41 color process as described in, for example, the British Journal of Photography Annual of 1988, pages 196–198. To obtain a positive (or reverse) image, the color development step can be preceded by development with a non-chromogenic developing agent to develop exposed silver halide but not form dye, and then uniformly fogging the element to render unexposed silver halide developable, followed by development with a chromogenic developer. Alternatively, a direct-positive emulsion can be employed to obtain a positive image.

Development is followed by the conventional steps of bleaching, fixing, or bleach-fixing to remove silver and silver halide, washing and drying. Bleaching and fixing can be performed with any of the materials known to be used for that purpose. Bleach baths generally comprise an aqueous solution of an oxidizing agent such as water soluble salts and complexes of iron (III) (such as potassium ferricyanide, ferric chloride, ammonium or potassium salts of ferric ethylenediaminetetraacetic acid), water-soluble dichromates (such as potassium, sodium, and lithium dichromate), and the like. Fixing baths generally comprise an aqueous solution of compounds that form soluble salts with silver ions, such as sodium thiosulfate, ammonium thiosulfate, potassium thiocyanate, sodium thiocyanate, thioureas, and the like.

The invention is further illustrated by the following examples, without being limited thereby. In the examples, the pKa values of the dyes were determined in 3% Triton X-100/water micelles having an ionic strength of 0.375. The Triton-X (Scintillation Grade) was purchased from Rohm & Haas Co. Triton-X is a non-ionic surfactant. The measurement of physical parameters using Triton-X micellular conditions is known from, for example, L. K. J. Tong and M. C. Glesmann, *J. Am. Chem. Soc.*, 79 4310 (1957).

EXAMPLE 1

This example describes the preparation of a cyan dye which is a species falling within the above structures I, 3, and 6, according to the present invention.

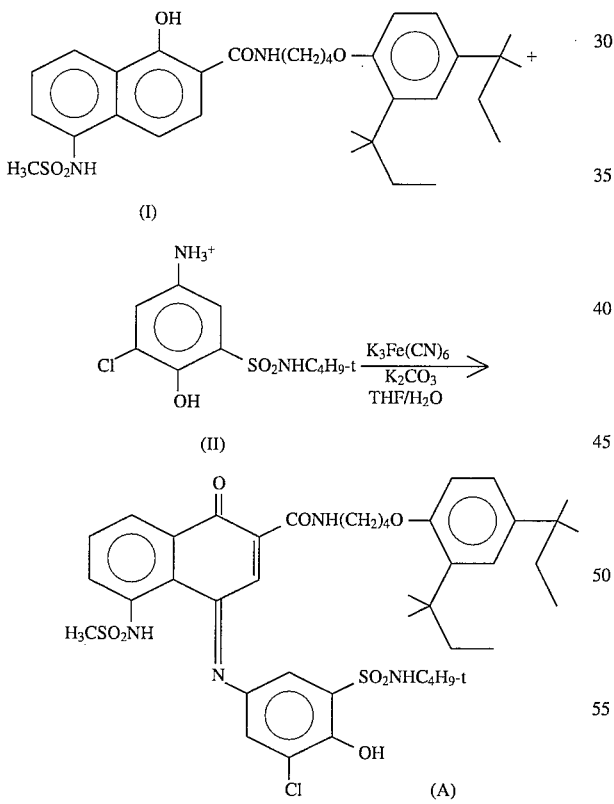

Compound I was prepared as follows:

5-Acetamido-1-naphthol (prepared by acetylation of 5-amino-1-naphthol using acetic anhydride) was car-boxylated via the Kolbe-Schmitt Reaction to give 5-acetamido-1-hydroxy-2-naphthoic acid. The acetyl group was removed via aqueous hydroxide to give 5-amino-1-hydroxy-2-naphthoic acid. This compound was then trimesylated by treatment with methanesulfonic anhydride. Two of the mesyl groups were removed by aqueous hydroxide to give 1-hydroxy-5-methanesulfonamido-2-naphthoic acid. The acid chloride of this carboxylic acid was formed using thionyl chloride in ethyl acetate. This acid chloride was reacted with 4-(2',4'-ditertiary amyl phenoxy) butylamine to give the coupler.

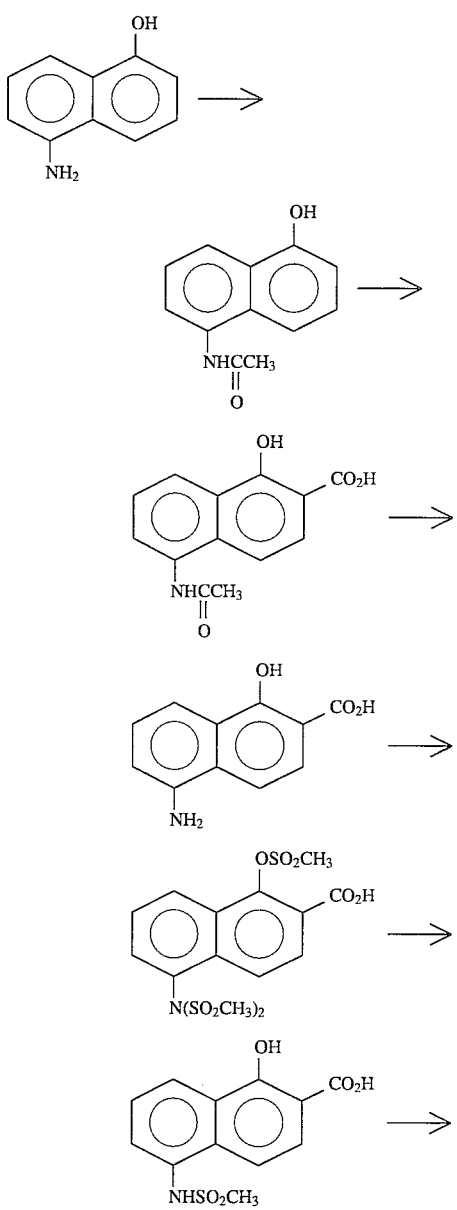

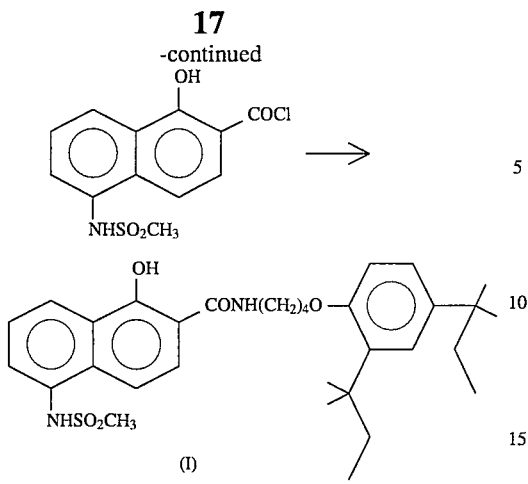

(I)

Compound II was prepared as follows:

2-Chloro-6-chlorosulfonylphenyl methanesulfonate was treated with t-butylamine and then base to give N-t-butyl 3-chloro-2-hydroxybenzenesulfonamide. Without purification, this material was nitrated using nitric acid in acetic acid to give N-t-butyl 3-chloro-2-hydroxy-5-nitrobenzenesulfonamide. Using sodium dithionite, this compound was reduced to give the aminophenol. The hydrochloride salt of this has also been prepared.

Dye A was prepared as follows:

18g of (I) and 10g of (II) were dissolved in 400 ml of stirred TMF. 120 g of $K_3Fe(CN)_6$ was dissolved in 400 ml of $H_2O$ (Solution A) and 80 g of $K_2CO_3$ was dissolved in 400 ml of $H_2O$ (Solution B). Solution B was added to the stirred THF solution, followed by the addition of Solution A. The resulting solution was stirred for 15 minutes. A 10% aq. HCl solution was added until a pH of about 1–2 was obtained. It was extracted with three 500 ml portions of $Et_2O$. The $Et_2O$ extracts were combined and evaporated. The residue was dissolved in 200 ml of AcOH. The AcOH solution was added to 800 ml of rapidly stirred $H_2O$. The precipitate was collected and dried at 1 mm pressure overnight in a vacuum oven. This procedure yielded 23 g of a red-maroon solid (A) having a pKa of about 3.7–3.8.

EXAMPLE 2

The following dye having a structure within the scope of above generic structures I, 3, and 6 and a pKa of about 3.6 has been prepared using a procedure as in Example 1. Compound III was prepared as follows: 5-(methanesulfonyl)amino-2-chlorosulfonylnaphthyl methanesulfonate was treated with di-n-hexylamine and then hydroxide to give N,N-di-n-hexyl-1-hydroxymethylsulfonylamino-2-naphthyl-sulfonamide.

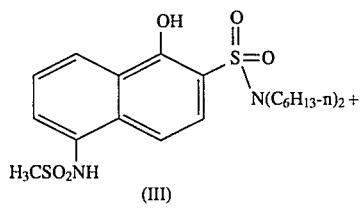

(III)

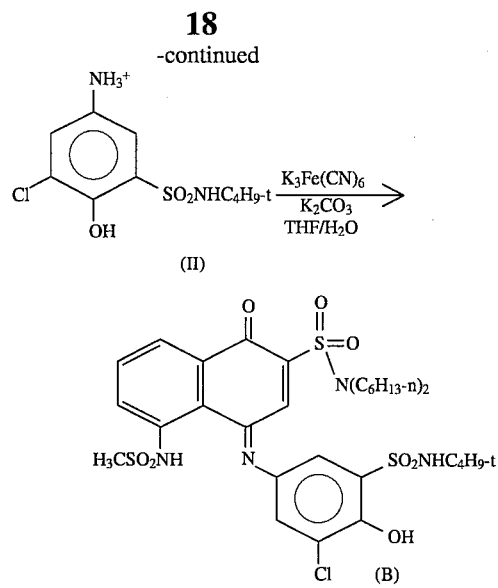

(B)

The following cyan dyes have also been prepared using procedures analogous to those of Examples 1 and 2. The procedures comprised dissolving the appropriate coupler and developer in THF with stirring, adding aqueous sodium carbonate, and then adding aqueous potassium ferricyanide. After stirring, the resultant mixture was extracted with ether and washed with water. If necessary, the dye was purified by silica gel column chromatography.

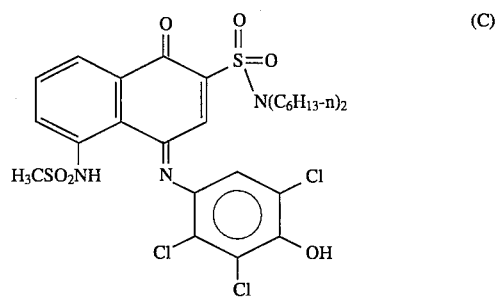

(C)

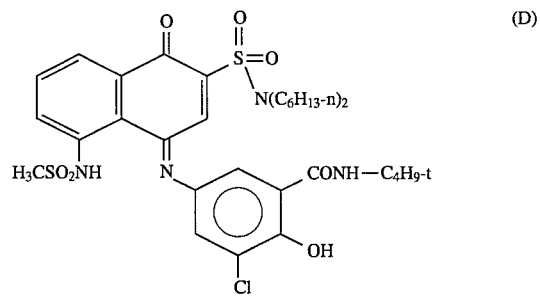

(D)

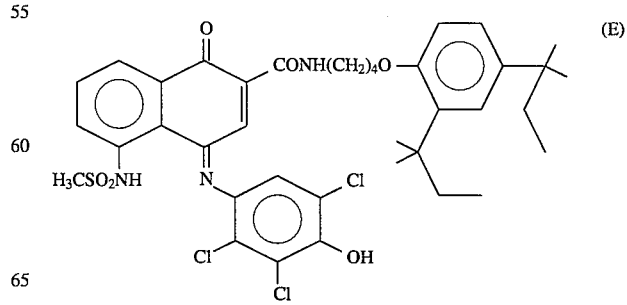

(E)

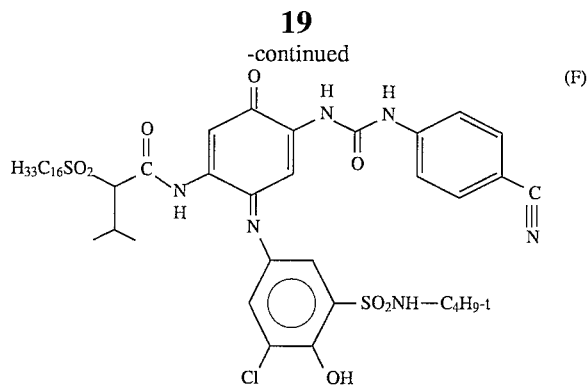

Dyes (C), (D), and (E) are species of Structure 3, and dye (F) is a species of Structure 2. Dye C has a pKa value of about 4.43; dye D of about 4.81; dye E of about 4.32, and dye F of about 4.93.

EXAMPLE 3

This example represents the preparation of a one-equivalent cyan coupler which will release the cyan dye prepared in Example 1 when reacted with oxidized silver halide.

orange band was collected. This orange material was evaporated and redissolved in a minimal amount of $Et_{20}$. Petroleum ether (bp 30–60) was added with stirring to precipitate a gooey oil (not collected, it stuck to the walls of the flask) and then a fluffy solid. This fluffy solid was rapidly and carefully collected via filtration. The ether/petroleum ether recrystallization was repeated two additional times. This procedure yielded 2.0 g of orange powder. Mass spec. and $^1$H-NMR were consistent with the above structure. HPLC indicated that it was 95% pure.

The following one-equivalent couplers which release a low pKa cyan dye can also be prepared in an analogous procedure:

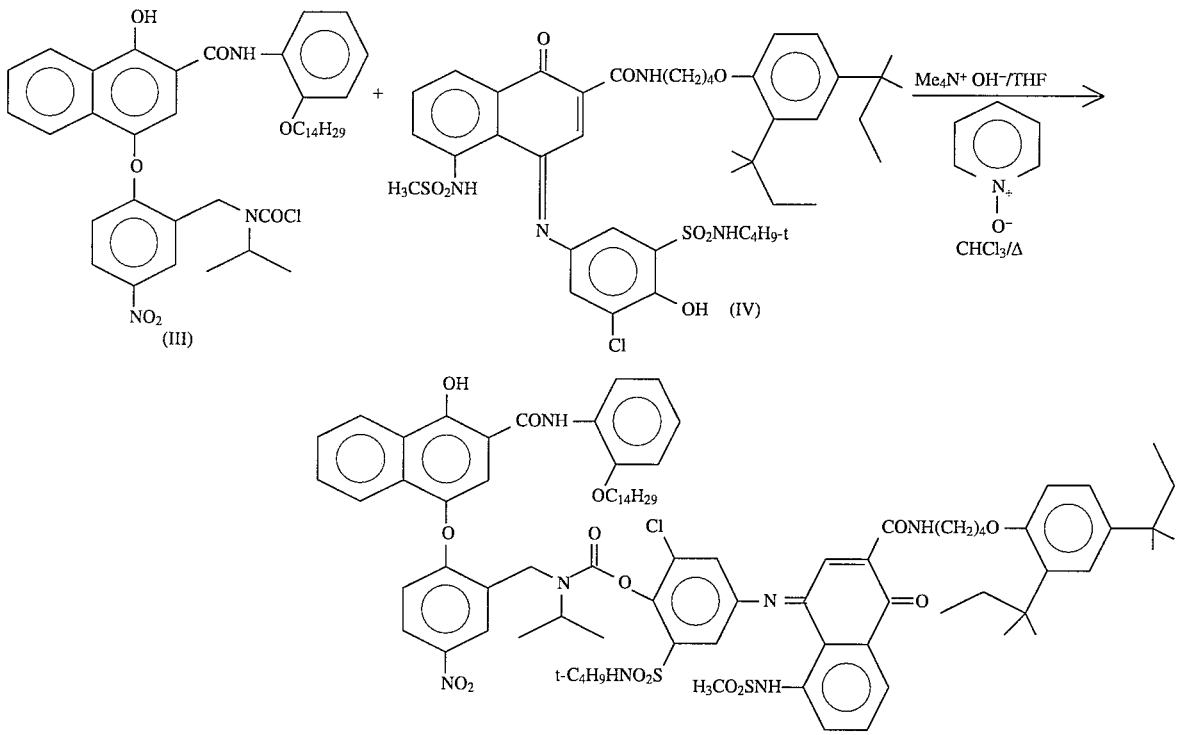

5.0 g Of (IV), the dye prepared in Example I(A), and 1.0 g of $Me_4N^+OH.5H_2O$ were dissolved in 50 ml of THF. The volatiles were evaporated, and the residue was redissolved in 100 ml $CHCl_3$. 5 g of (III) and 0.5 g of pyridine N-oxide (purified by sublimation) were added to the solution. It was heated at reflux for 3 days, then cooled and evaporated. The residue was chromatographed twice on 500 g portions of silica gel using 10% $CH_3CN$/90% toluene as eluent. The

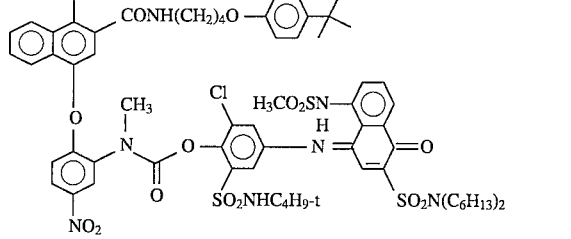

This compound releases the dye prepared in Example 1.
The following compound, H, releases dye (F):

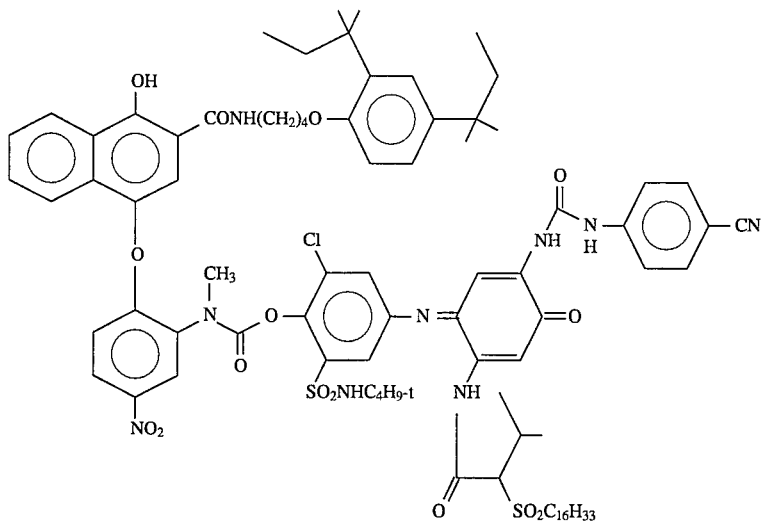

(H)

Compounds I and J release dye (E).

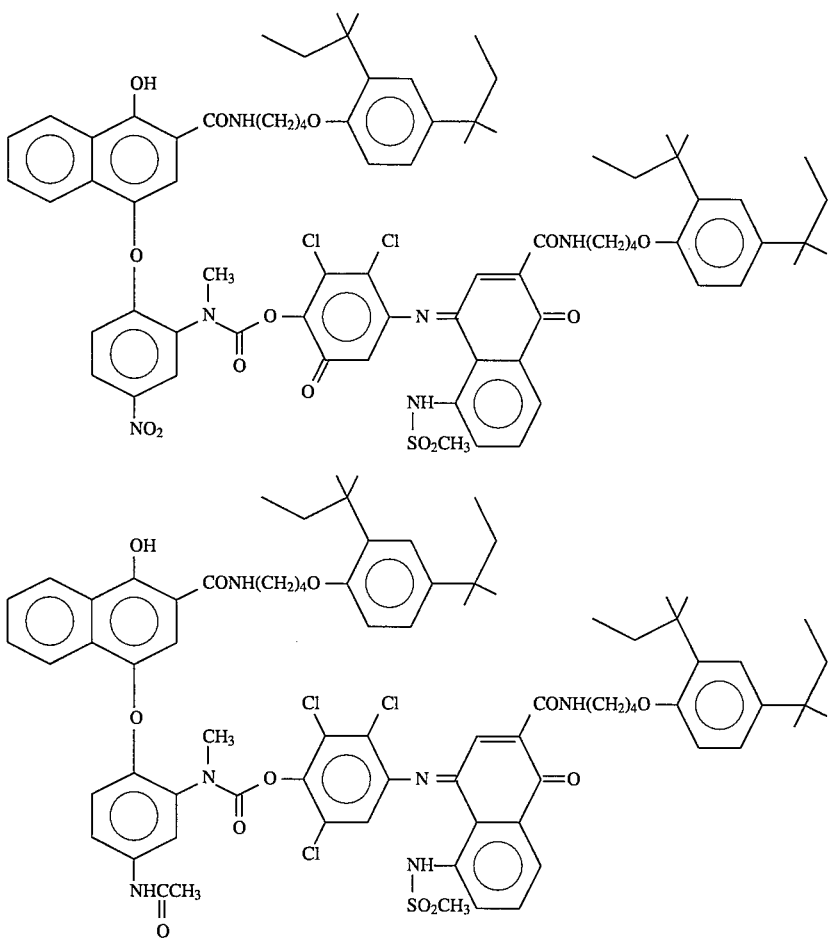

(I)

(J)

EXAMPLE 4

The following low pKa oxochromic magenta dyes, (K)–(O), have been produced. These dyes are hypochromically shifted when blocked on the developer oxygen and, when released, are ionized in film coatings without the use of a mordant. They have high acidities in the film coating. Dye (K) has a pKa of about 2.7, dye (L) of about 1.7, dye (M) of about 2.9, dye (N) of about 1.8 and dye (O) of about 3.6. Dyes (K) through (N) are species falling within generic structure 4, and dye (O) is a species falling within generic structure 5.

Dye (O) was prepared as follows. Dyes (K)–(N) were prepared in an analogous manner.

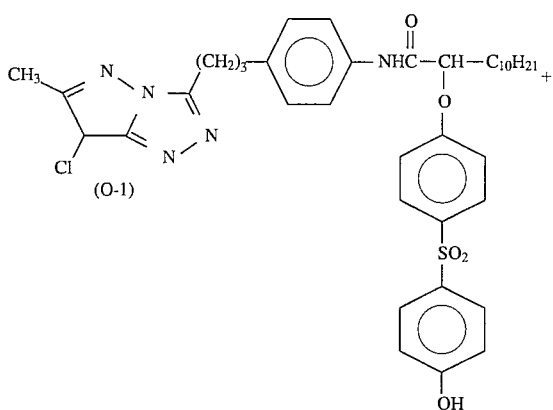

(O-1)

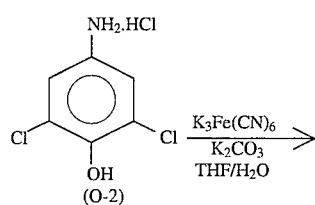

(O-2)

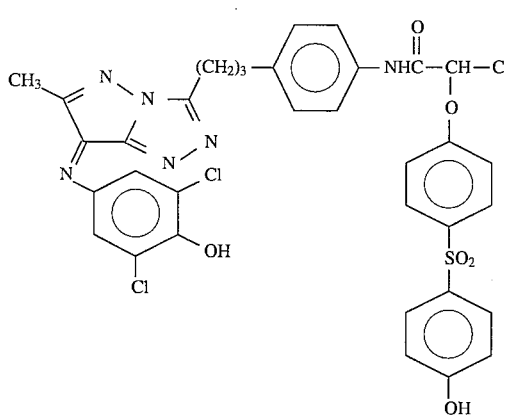

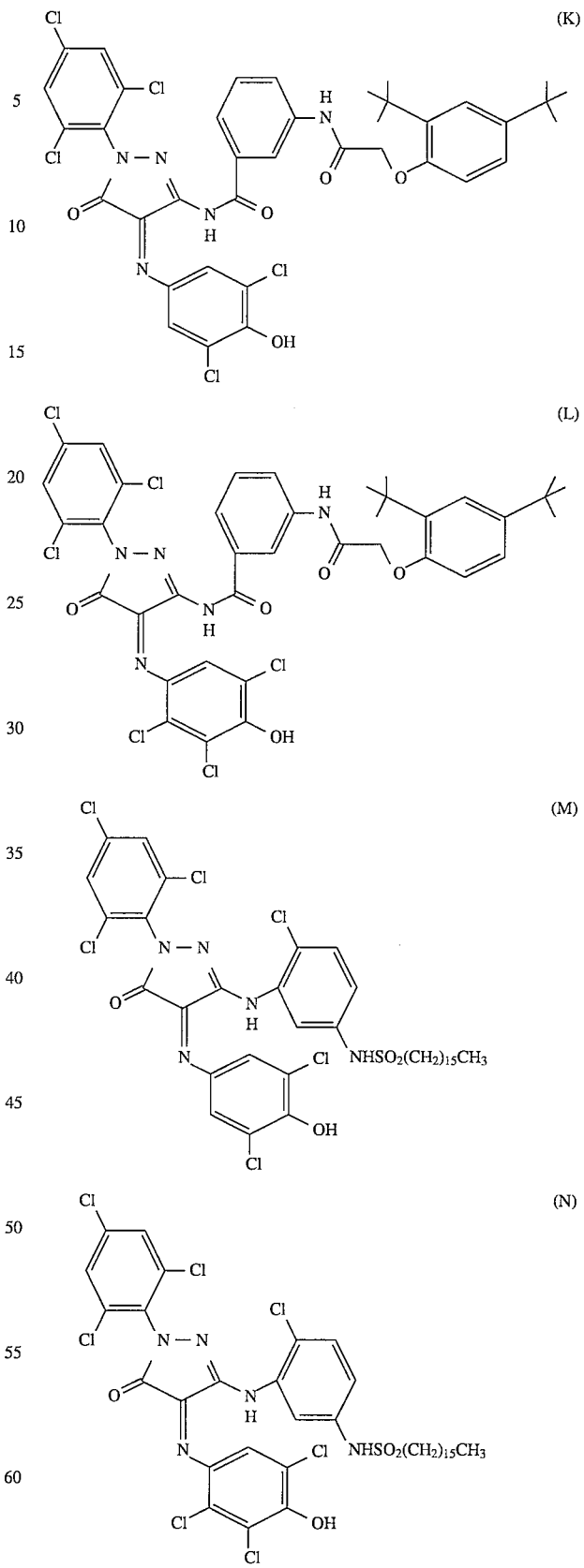

To a rapidly stirred solution of 10.8 g of coupler (O-1) and 3.2 g of developer (O-2) in 250 ml of wet tetrahydrofuran was added all at once, a solution of 26.3 g of potassium ferricyanide and 17.0 g of potassium carbonate dissolved in 250 ml of water. After ten minutes, the reaction mixture was extracted with ethyl acetate. The organic phase was then washed with 5% aqueous hydrochloric acid. After separation of the layers, the organic phase was dried over anhydrous magnesium sulfate and then evaporated to an oil. This oil was solidified by stirring with acetonitrile. The solid was then recrystallized twice from methanol to give 8.7 g of dye (O) of approximately 90% purity. The proton NMR was consistent with the proposed structure.

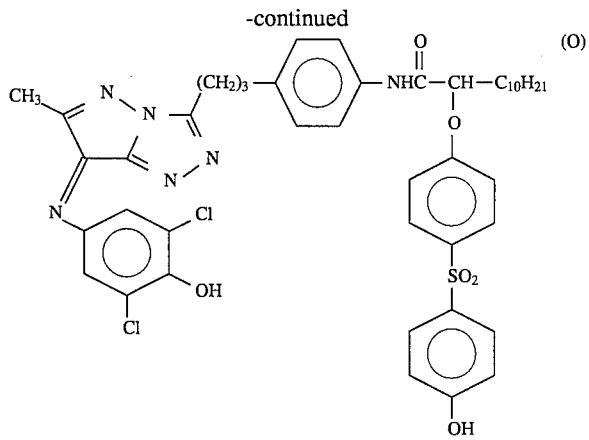

The pKa values of dyes (K)–(O) were determined as follows:

A $2.5 \times 10^{-6}$ tool portion of the dye was combined with 3 ml (3.18 g) of Triton X-100 in a 50 ml volumetric flask. Approximately 2 ml methylene chloride was added to dissolve the dye in the Triton X-100; the methylene chloride was then vaporized with a stream of nitrogen. Approximately 25 ml water was added, and the sample was vigorously agitated with a vortex mixer to form micelles, then diluted to the mark. Mixtures of the micelle solution and phosphate buffers (1:1 volume/volume ratio) were prepared, and measurements were made of the pH and the absorbance at the wavelength corresponding to the maximum visible absorbance of the ionized dye. The observed absorbance ($D_{obs}$) versus pH data was then fit by non-linear regression to the expression $$pKa = pH + \log\left[(D_{base} - D_{obs})/(D_{obs} - D_{acid})\right]$$

where $D_{base}$ is the density of the totally ionized form, and $D_{acid}$ is the density of the totally non-ionized form. By this method a value for the pKa and an associated standard deviation are calculated. The pKa for the dyes is as set forth previously.

Each of the dyes K–O was fully ionized in a photographic film. The fact the dyes remained fully ionized was established as follows.

0.14 g/m² of DYE, dispersed at twice its weight in dibutylphthalate, was coated with 4.86 g/m² gelatin, 2% by volume surfactant (IOG, a non-ionic surfactant, commercially available from Olin) with formaldehyde hardener (0.5% by weight of gel) on a clear polyester support.

The resulting coating were monitored spectrophotometrically for protonated and ionized forms of the dye (which usually differ in $L_{max}$ by 20–50 nm). The pH of the coating can be adjusted by soaking in appropriate buffers.

With the inventive dyes, no protonated forms of the dye were detected, even when the pH of the coating was adjusted to pH 5 with buffer.

EXAMPLE 5

To demonstrate the photographic utility of the dyes of the present invention, the couplers which release the dyes were coated in the following format.

Single layer photographic elements were prepared by coating a cellulose acetate-butyrate film support (with a rem-jet antihalation backing) with a photosensitive layer containing a silver bromoiodide emulsion at 1.61 g/m², gelatin at 3.77 g/m² and the coupler was dispersed in half its weight in dibutylphthalate at 0.063 mmol/ft². The photosensitive layer was overcoated with a layer containing gelatin at 2.69 g/m² and bis-vinylsulfonyl methyl ether hardener at 1.75 weight percent based on total gel.

Samples of each element were exposed imagewise through a stepped density test object and busjected to the KODAK FLEXICOLOR (C41) process as described in *British Journal of Photography Annual.* 1988, pp. 196–198.

The results are shown in Table 1.

TABLE 1

| Compound | Level (mmol/ft²) | Red $D_{min}$ | Red $D_{max}$ | Gamma |
|---|---|---|---|---|
| I | .063 | .08 | .38 | .13 |
| J | .063 | .11 | 1.04 | .43 |
| H | .063 | .04 | .49 | .28 |
| G | .063 | .10 | 1.00 | .57 |
| Compound prepared in Example 3 | .063 | .05 | 1.32 | 1.33 |

Dmax is the red density at maximum exposure and Gamma is the maximum slope between any two exposure steps.

This data demonstrates that compounds of this invention are useful in photographic systems. There was no evidence in the above coatings of the presence of the protonated form of the azaphenolic dye.

Comparative Example 1

This is a comparative example of prior art yellow one-equivalent couplers which release an azophenol dye. Couplers P and Q were coated in the same format as Example 5.

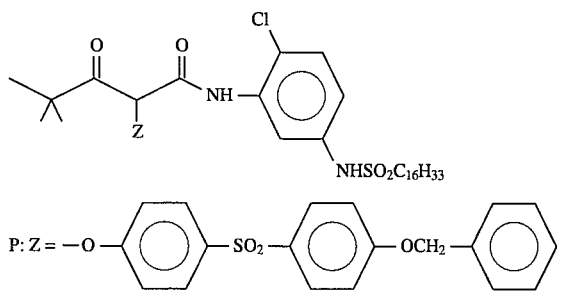

Q: Z = 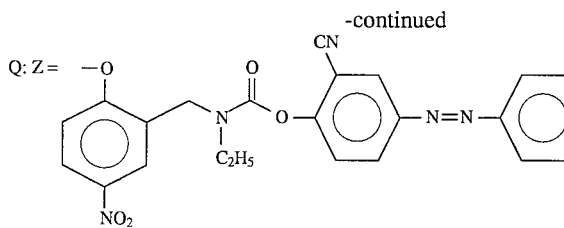

-continued

Coupler P is a non-dye containing conventional coupler. Compound Q is a prior art yellow one-equivalent coupler which releases a ballasted azophenol dye through a timing group. This dye has a pKa of 8.

The data in Table 2 demonstrate that not all of the dye in compound Q was ionized after release during the process. Here the dye gives an undesirable shift in hue due to the presence of ionized and non-ionized dye.

TABLE 2

| Compound | Amount (mmol/ft²) | Blue $D_{max}$ | $D_{max}$ after post-treatment with CETAB (Cetyltriethylammonium bromide) |
|---|---|---|---|
| P | 0.063 | 1.79 | 1.88 (not much change) |
| Q | 0.063 | 1.39 | 2.66 (big increase in blue density) |

The invention has been described in detail with particular reference to preferred embodiments thereof, but it will be understood that variations and modifications can be effected within the spirit and scope of the invention.

What is claimed is:

1. A photographic element comprising a support, and a silver halide emulsion layer having associated therewith a molecule which is a one-equivalent coupler having the structure COUP—(CONNECT)$_{n'}$—(T)$_m$—DYE wherein n' is 0 or 1, m is 0, 1, or 2, COUP is a coupler moiety, CONNECT is a group attached to a coupling site of the coupler that connects the coupler to either the timing group T or directly to the dye, if attached directly to the dye it remains permanently attached to the dye after the dye is released from COUP, T is a timing group, which is cleaved from the dye during processing, DYE is a dye having the following structure,

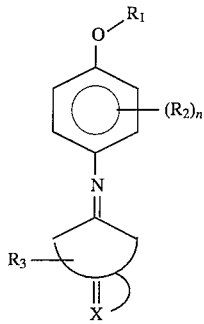

wherein, $R_1$=H, a removable timing group, or a removable blocking group, wherein removable denotes that after processing, $R_1$ is hydrogen, so that the dye remains substantially or completely ionized in the element, $R_2$=one or more substituents, which ensure that the oxygen auxochrome group remains ionized after processing of the element, n=1, 2, 3 or 4, X=O or N; wherein if X is N then it is part of a heterocyclic ring that forms part of the dye chromophore,

represents a carbon containing ring or ring system, $R_3$=one or more substituents, which may be located anywhere along the ring or ring system, the

indicates that if X is N, then it is part of the ring or ring system;

with the proviso that the substituent $R_2$ and $R_3$ and the ring or ring system are selected so that the dye has a pKa below about five so that the dye remains fully ionized or substantially ionized in the processed photographic element such that the dye retains the desired hue;

and with the further proviso that the molecule may optionally contain one or more ballast groups, wherein said dye is a yellow dye, or a cyan dye, or has the structure

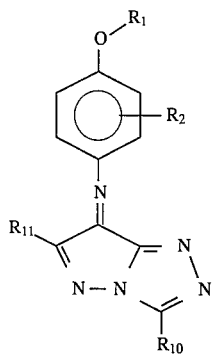

wherein, $R_{10}$ and $R_{11}$ are independently selected from a substituted alkyl, substituted alkyloxy or substituted phenyl group.

2. A photographic element as claimed in claim 1, wherein $R_2$ is an electron withdrawing group.

3. A photographic element as claimed in claim 2, wherein an $R_2$ substituent is present in both the 2 and 6 positions, both $R_2$ substituents being electron-withdrawing groups, which may be the same or different.

4. A photographic element as claimed in claim 3, wherein said electron-withdrawing groups are selected from nitro, Cl, CN, $SO_2N(R')_2$, $CON(R')_2$, $CO_2R'$, wherein R' is hydrogen or an alkyl or aryl group.

5. A photographic element as claimed in claim 4, wherein said electron withdrawing groups are selected from the group consisting of Cl, $SO_2NH(t\text{---}Bu)$, and $C(O)NH2$.

6. A photographic element as claimed in claim 1, wherein said dye has a pKa of below 4.

7. A photographic element as claimed in claim 1, wherein said dye has the structure

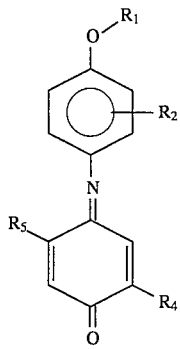

wherein, $R_4$ and $R_5$ are selected from —NHCOR' or —NHCON(R')$_2$, wherein R' is hydrogen or a substituted or unsubstituted alkyl group or substituted or unsubstituted phenyl group.

8. A photographic element as claimed in claim 1 when said dye has the structure

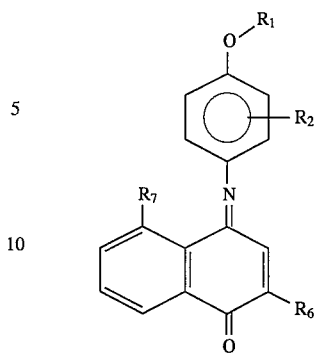

wherein, $R_6$ is an electron-withdrawing group, and $R_7$ is a group capable of hydrogen bond donation to the imine nitrogen.

9. A photographic element as claimed in claim 8, wherein $R_6$ is selected from the group consisting of Cl, $SO_2N(R')_2$, CN, $SO_2R'$, $CON(R')_2$, $CO_2R'$, and CONHR', wherein R' is hydrogen or an alkyl or phenyl group either of which may be substituted or unsubstituted, and $R_7$ is OH or an NH acidic group selected from the group consisting of —NHCOR', —NHCON(R')$_2$, —NHSO$_2$R', and —NHSO$_2$N(R')$_2$, wherein R' is as defined for $R_6$.

10. A photographic element as claimed in claim 1, wherein said dye has the structure

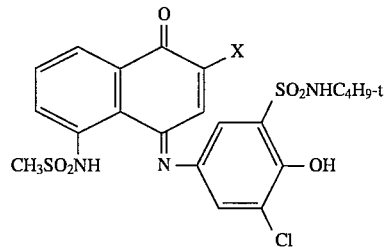

wherein,

X=—CONHR' or —SO$_2$N(R')$_2$, wherein R' is an alkyl or phenyl group, either of which may be substituted or unsubstituted.

11. A photographic element as claimed in claim 1, wherein said dye is selected from the following compounds A–F:

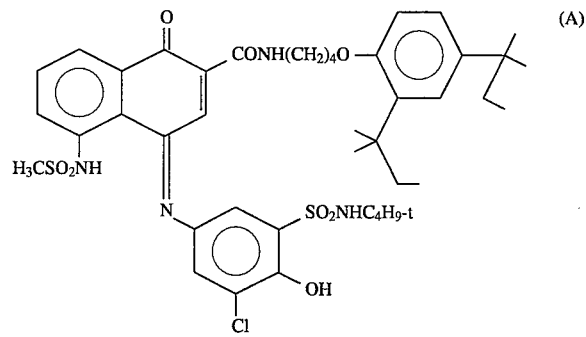

(A)

-continued

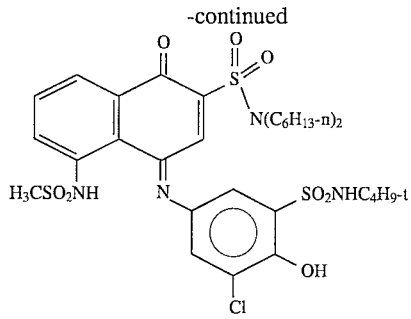
(B)

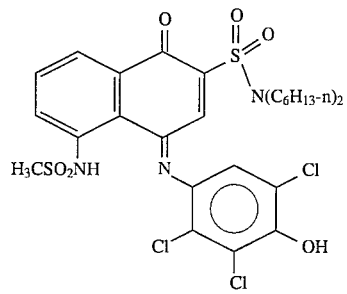
(C)

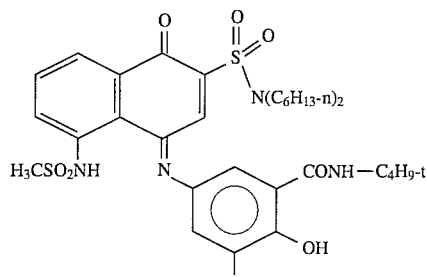
(D)

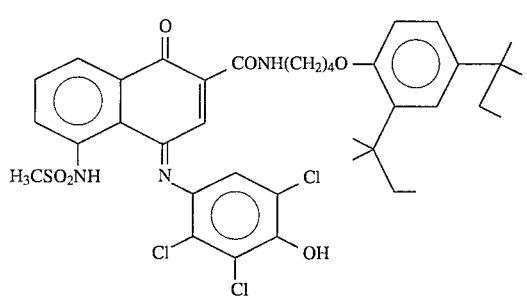
(E)

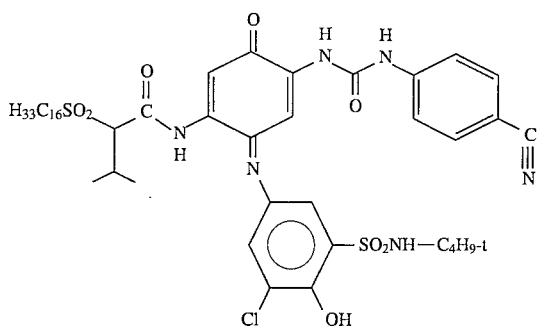
(F)

12. A photographic element as claimed in claim 1, wherein said COUP is a universal coupler.

13. A photographic element as claimed in claim 1, wherein said COUP is a pyrazolotriazole.

14. A photographic element as claimed in claim 13, wherein COUP is a 1H-pyrazolo (1,5-b) (1,2,4) triazole or 1H-pyrazolo (2,3,-c) (1,2,4) triazole.

15. A photographic element as claimed in claim 1, wherein no mordant is present in the element.

16. A photographic element as claimed in claim 1, wherein the DYE is a yellow dye.

17. A photographic element as claimed in claim 1, wherein the DYE is a cyan dye.

18. A photographic element as claimed in claim 1, wherein the DYE is a magenta dye.

19. A photographic element as claimed in claim 1, wherein a ballast group is attached to a portion of the molecule which is intended to remain in the film after reaction with oxidized silver halide developer.

20. A photographic element as claimed in claim 1, wherein COUP is other than a magenta dye-forming coupler.

21. A photographic element as claimed in claim 1, wherein the DYE remains substantially in the layer in the element in which it is generated.

22. A photographic element comprising a support, and a silver halide emulsion layer having associated therewith a molecule which is a one-equivalent coupler having the structure COUP—(CONNECT)$_{n'}$—(T)$_m$—DYE wherein n' is 0 or 1, m is 0, 1, or 2, COUP is a 1H-pyrazolo (2,3-C)(1,2,4)triazole, CONNECT is a group attached to a coupling site of the coupler that connects the coupler to either the timing group T or directly to the dye, if attached directly to the dye it remains permanently attached to the dye after the dye is released from COUP, T is a timing group, which is cleaved from the dye during processing, DYE is a dye having the following structure,

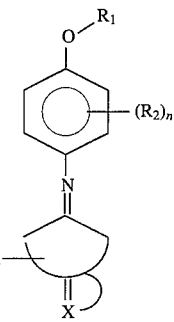
(I)

wherein, $R_1$=H, a removable timing group, or a removable blocking group, wherein removable denotes that after processing, $R_1$ is hydrogen, so that the dye remains substantially or completely ionized in the element, $R_2$=one or more substituents, which ensure that the oxygen auxochrome group remains ionized after processing of the element, n=1, 2, 3 or 4, X=O or N; wherein if X is N then it is part of a heterocyclic ring that forms part of the dye chromophore,

represents a carbon containing ring or ring system, $R_3$=one or more substituents, which may be located anywhere along the ring or ring system, the indicates that if X is N, then it is part of the ring or ring system;

with the proviso that the substituents $R_2$ and $R_3$ and the ring or ring system are selected so that the dye has a pKa below about five so that the dye remains fully ionized or substantially ionized in the processed photographic element such that the dye retains the desired hue;

and with the further proviso that the molecule may optionally contain one or more ballast groups.

23. A multicolor photographic element comprising a support bearing a cyan dye image-forming unit comprising at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler and a yellow dye image-forming unit comprising at least one blue-sensitive silver halide emulsion layer having associated therewith at least one yellow dye forming coupler, wherein the element further comprises a molecule having a structure COUP—(CONNECT)$_{n'}$—(T)$_m$—DYE wherein n' is 0 or 1, m is 0, 1, or 2, COUP is a coupler moiety, CONNECT is a group attached to a coupling site of the coupler that connects the coupler to either the timing group T or directly to the dye, if attached directly to the dye it remains permanently attached to the dye after the dye is released from COUP, T is a timing group, which is cleaved from the dye during processing, DYE is a dye having the following structure,

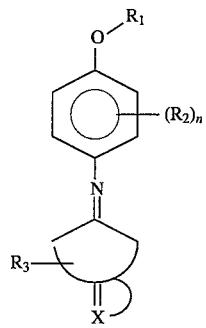

(I)

wherein, $R_1$=H, a removable timing group, or a removable blocking group, wherein removable denotes that after processing, $R_1$ is hydrogen, so that the dye remains substantially or completely ionized in the element, $R_2$=one or more substituents, which ensure that the oxygen auxochrome group remains ionized after processing of the element, n=1, 2, 3 or 4, X=O or N; wherein if X is N then it is part of a heterocyclic ring that forms part of the dye chromophore,

represents a carbon containing ring or ring system, $R_3$=one or more substituents, which may be located anywhere along the ring or ring system, the indicates that if X is N, then it is part of the ring or ring system;

with the proviso that the substituents $R_2$ and $R_3$ and the ring or ring system are selected so that the dye has a pKa below about five so that the dye remains fully ionized or substantially ionized in the processed photographic element such that the dye retains the desired hue;

and with the further proviso that the molecule may optionally contain one or more ballast groups, wherein said dye is a yellow dye, or a cyan dye, or has the structure

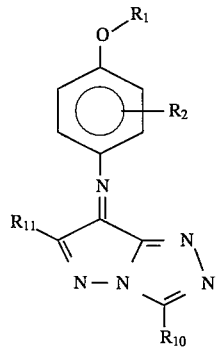

wherein, $R_{10}$ and $R_{11}$ are independently selected from a substituted alkyl, substituted alkyloxy or substituted phenyl group.

24. A process for developing an image in a photographic element comprising a support and a silver halide emulsion containing an image-wise distribution of developable silver halide grains, said process comprising the step of developing said element with a silver halide color developing agent in the presence of a molecule having a structure COUP—(CONNECT)$_{n'}$—(T)$_m$—DYE wherein n' is 0 or 1, m is 0, 1, or 2, COUP is a coupler moiety, CONNECT is a group attached to a coupling site of the coupler that connects the coupler to either the timing group T or directly to the dye, if attached directly to the dye it remains permanently attached to the dye after the dye is released from COUP, T is a timing group, which is cleaved from the dye during processing, DYE is a dye having the following structure,

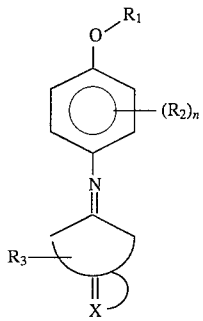

(I)

wherein, $R_2$=H, a removable timing group, or a removable blocking group, wherein removable denotes that after processing, $R_1$ is hydrogen, so that the dye remains substantially or completely ionized in the element, $R_2$=one or more substituents, which ensure that the oxygen auxochrome group remains ionized after processing of the element, n=1, 2, 3 or 4, X=O or N; wherein if X is N then it is part of a heterocyclic ring that forms part of the dye chromophore,

represents a carbon containing ring or ring system, $R_3$=one or more substituents, which may be located anywhere along the ring or ring system,

the indicates that if X is N, then it is part of the ring or ring system;

with the proviso that the substituents $R_2$ and $R_3$ and the ring or ring system are selected so that the dye has a pKa below about five so that the dye remains fully ionized or substantially ionized in the processed photographic element such that the dye retains the desired hue;

and with the further proviso that the molecule may optionally contain one or more ballast groups, wherein said dye is a yellow dye, or a cyan dye, or has the structure

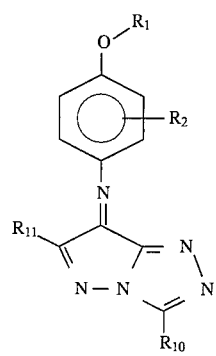

wherein, $R_{10}$ and $R_{11}$ are independently selected from a substituted alkyl, substituted alkyloxy or substituted phenyl group.

25. A photographic silver halide emulsion containing a molecule

COUP—(CONNECT)$_{n'}$—(T)$_m$—DYE wherein n' is 0 or 1, m is 0, 1, or 2,

COUP is a coupler moiety,

CONNECT is a group attached to a coupling site of the coupler that connects the coupler to either the timing group T or directly to the dye, if attached directly to the dye it remains permanently attached to the dye after the dye is released from COUP, T is a timing group, which is cleaved from the dye during processing, DYE is a dye having the following structure,

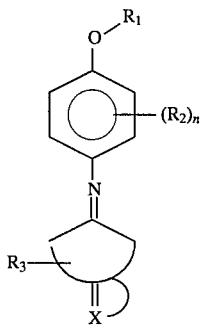 (I)

wherein $R_1$=H, a removable timing group, or a removable blocking group, wherein removable denotes that after processing, $R_1$ is hydrogen, so that the dye remains substantially or completely ionized in the element, $R_2$=one or more substituents, which ensure that the oxygen auxochrome group remains ionized after processing of the element, n=1, 2, 3 or 4, X=O or N; wherein if X is N then it is part of a heterocyclic ring that forms part of the dye chromophore,

represents a carbon containing ring or ring system, $R_3$=one or more substituents, which may be located anywhere along the ring or ring system, the

indicates that if X is N, then it is part of the ring or ring system;

with the proviso that the substituents $R_2$ and $R_3$ and the ring or ring system are selected so that the dye has a pKa below about five so that the dye remains fully ionized or substantially ionized in the processed photographic element such that the dye retains the desired hue;

and with the further proviso that the molecule may optionally contain one or more ballast groups, wherein said dye is a yellow dye, or a cyan dye, or has the structure

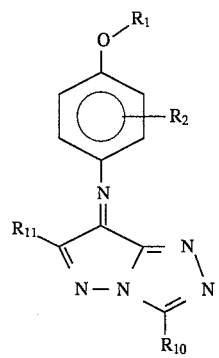

wherein, $R_{10}$ and $R_{11}$ are independently selected from a substituted alkyl, substituted alkyloxy or substituted phenyl group.

26. A photographic element comprising a support, and a silver halide emulsion layer having associated therewith a molecule which is a one-equivalent coupler having the structure

COUP—(CONNECT)$_{n'}$—(T)$_m$—DYE wherein n' is 0 or 1, m is 0, 1, or 2,

COUP is a coupler moiety,

CONNECT is a group attached to a coupling site of the coupler that connects the coupler to either the timing group T or directly to the dye, if attached directly to the dye it remains permanently attached to the dye after the dye is released from COUP, T is a timing group, which is cleaved from the dye during processing, DYE is a dye having the following structure,

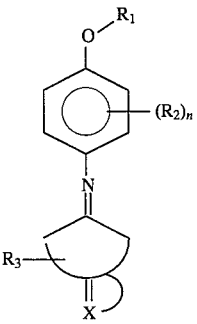 (I)

wherein, $R_1$=H, a removable timing group, or a removable blocking group, wherein removable denotes that after processing, $R_1$ is hydrogen, so that the dye remains substantially or completely ionized in the element, $R_2$=one or more substituents, which ensure that the oxygen auxochrome group remains ionized after processing of the element, n=1, 2, 3 or 4, X=O or N; wherein if X is N then it is part of a heterocyclic ring that forms part of the dye chromophore,

represents a carbon containing ring or ring system, $R_3$=one or more substituents, which may be located anywhere along the ring or ring system, the

indicates that if X is N, then it is part of the ring or ring system;

with the proviso that the substituents $R_2$ and $R_3$ and the ring or ring system are selected so that the dye has a pKa below about five so that the dye remains fully ionized or substantially ionized in the processed photographic element such that the dye retains the desired hue;

and with the further proviso that the molecule may optionally contain one or more ballast groups, wherein the DYE remains substantially in the layer in the element in which it is generated, and wherein COUP is other than a pyrazoloazole magenta dye-forming coupler.

27. A photographic element as claimed in claim 26, wherein said dye has the structure

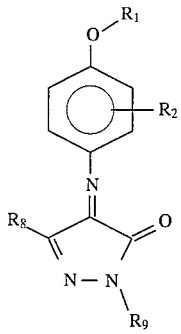

wherein, $R_8$ is selected from $NR'_2$, NH—Ph—R', NHCOR', or NH—Ph—NH—$SO_2$R', wherein R' is hydrogen or an alkyl or phenyl group, either of which may be substituted or unsubstituted, and $R_9$ is a substituted phenyl group.

28. A photographic element as claimed in claim 26, wherein said dye is selected from the following compounds (K)–(O)

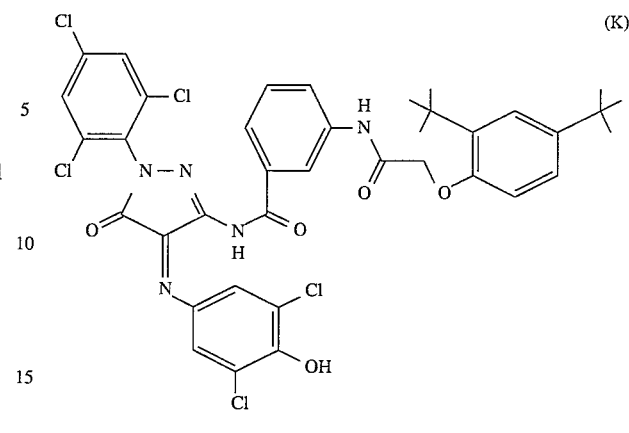

(K)

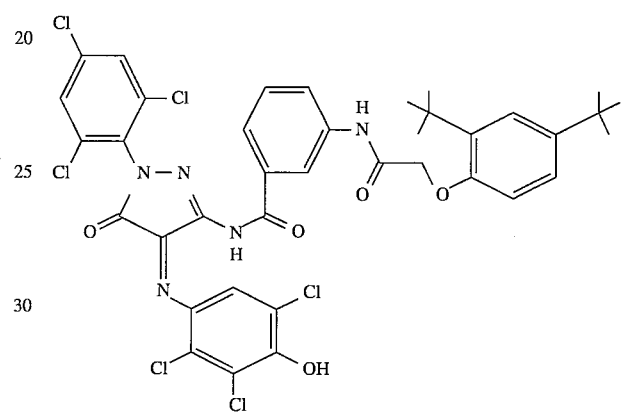

(L)

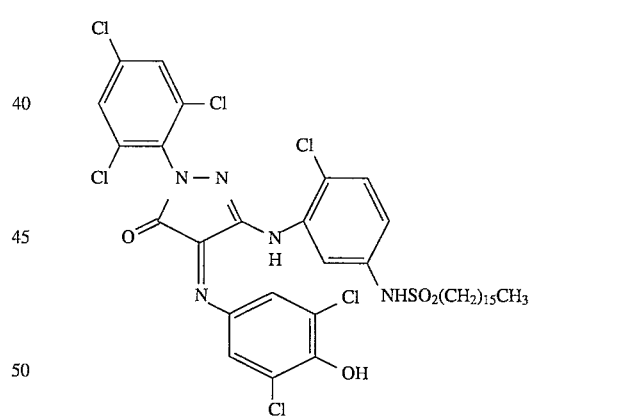

(M)

41
-continued
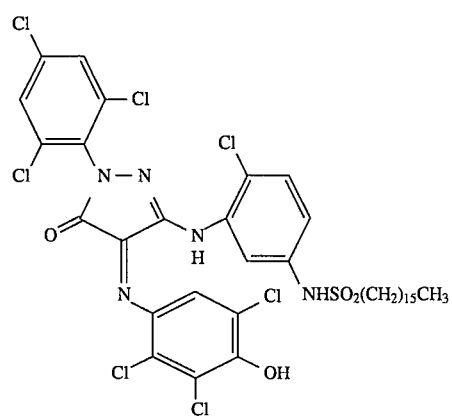
42
-continued
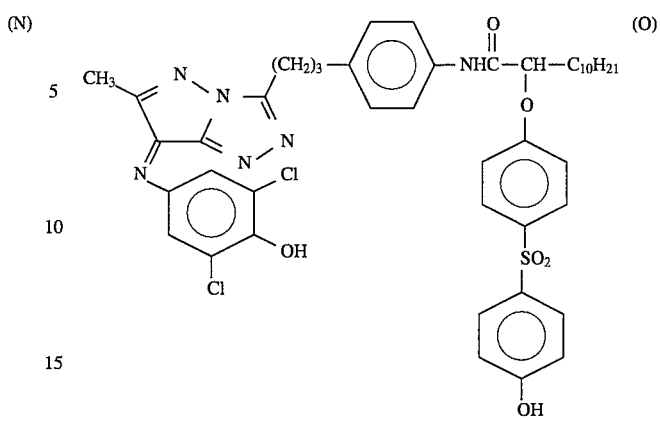
* * * * *